United States Patent [19]

Mori

[11] Patent Number: 4,804,240

[45] Date of Patent: Feb. 14, 1989

[54] LIGHT RAY RADIATION DEVICE FOR USE IN MEDICAL TREATMENT

[76] Inventor: Kei Mori, 3-16-3-501, Kaminoge, Setagaya-ku, Tokyo, Japan

[21] Appl. No.: 107,698

[22] Filed: Oct. 9, 1987

[30] Foreign Application Priority Data

Dec. 22, 1986 [JP] Japan .................................. 61-306072

[51] Int. Cl.[4] .......................... A61N 5/06; G02B 6/00
[52] U.S. Cl. .................................. 350/96.10; 128/362; 128/377; 128/398
[58] Field of Search ...................... 350/96.10, 362, 377, 350/398, 395

[56] References Cited

U.S. PATENT DOCUMENTS

| | | | |
|---|---|---|---|
| 1,718,770 | 6/1929 | Zublin | 128/377 X |
| 1,916,561 | 7/1933 | Crosley | 128/398 X |
| 1,968,997 | 8/1934 | Drucker | 128/398 X |
| 3,417,746 | 12/1968 | Moore et al. | 128/398 X |
| 4,336,809 | 6/1982 | Clark | 128/398 X |
| 4,471,412 | 9/1984 | Mori | 362/32 |
| 4,646,743 | 3/1987 | Parris | 128/398 X |
| 4,653,472 | 3/1987 | Mori | 126/440 |
| 4,660,925 | 4/1987 | McCaughan, Jr. | 350/96.1 X |

*Primary Examiner*—John D. Lee
*Attorney, Agent, or Firm*—Jordan and Hamburg

[57] ABSTRACT

A light ray radiation device for use in medical treatment comprises an optical conductor cable, through which light rays corresponding to the visible light ray components of solar rays are transmitted. An elongated light radiator removably connected with the light-emitting end of the optical conductor cable, from which the light rays transmitted through the optical conductor cable, are almost uniformly discharged outside thereof. And a transparent cover member consisting of an almost hat-shaped elastic body, tightly covering the light radiator removably therefrom and which spreads out at its base portion.

3 Claims, 3 Drawing Sheets

LIGHT RAY RADIATION DEVICE FOR USE IN MEDICAL TREATMENT

BACKGROUND OF THE INVENTION

The present invention relates to a light ray radiation device for use in medical treatment, in particular, a visible light ray radiation device for use in medical treatment capable of radiating light ray components corresponding to the visible light rays of the sun onto the diseased part of a human body.

The present applicant has previously proposed various ways to focus solar rays or artificial light rays by the use of lenses or the like and to guide the same into an optical conductor cable thereby transmitting and emitting the same onto an optional desired place through the optical conductor. The solar rays or the artificial light rays transmitted and emitted in such a way are employed for illumination or other like purposes, for example, for cultivating plants, chlorella, or the like. In the process of doing the above, the visible light ray components of the solar rays containing therein neither ultraviolet nor infrared rays promote the health of a person by creating a living body reaction, or the same prevents the skin of a human from growing old. Furthermore, the visible light ray components have noticeable beneficial effects for recovering from arthritis, neuralgia, bedsores, rheumatism, injury scars, bone fracture scars, or the like, and for alleviating pain from those diseases. Such beneficial effects have been noticed by the present applicant.

On the basis of the above-mentioned discovery, the present application has previously proposed in various ways light ray radiation devices for use in medical treatment that are capable of giving beauty treatments or promoting the health of a human body by radiating the light rays that correspond to the visible light ray components of the sun which contain therein no harmful components such as ultraviolet rays, infrared rays, or the like.

A light ray radiation device for use in medical treatment previously proposed by the present application has an optical conductor cable, a semi-transparent cylindrical member furnished at the light-emitting end of the afore-mentioned optical conductor cable, and a cover member for closing one end of the cylindrical member. The solar rays or the artificial light rays are guided into the optical conductor cable at the end portion thereof, and the guided light rays are transmitted therethrough. The light rays corresponding to the visible light ray components of the sun's rays (the white-colored ones) are transmitted into the optical conductor cable in the manner previously proposed by the present applicant in various ways. The light-emitting end portion side of the optical conductor cable is attached to the cover member at approximately the central portion thereof. The solar ray energy transmitted through the optical conductor cable is discharged into the cylindrical member. At the time of administering medical treatment, the other end of the cylindrical member is put on the part of the patient to be treated, or the same is placed opposite that same part at the desired interval therefrom. The light rays consisting of the visible light ray components transmitted through the optical conductor cable in such a manner as mentioned before are radiated onto a diseased part, a desired portion, or another portion needing treatment. The light rays to be radiated onto a diseased part of a patient are the light rays corresponding to the visible light ray components of the sun's rays. Consequently, it becomes possible to administer medical treatment without exposing a patient to the harmful effects of ultraviolet or infrared rays.

SUMMARY OF THE INVENTION

The primary object of the invention is to provide a visible light ray radiation device for use in medical treatment capable of radiating light rays onto a specified diseased part of a human body from the light ray radiation device.

It is another object of the present invention to provide a visible light ray radiation device for use in medical treatment for piles, fungous tumor in the cavity or an injury scar caused by excising such a fungous tumor in the cavity.

It is another object of the present invention to provide a visible light ray radiation device for use in medical treatment capable of administering without giving the patient pain and allowing him (or her) to be very comfortable by being in a sitting position.

The above-mentioned features and other advantages of the present invention will be apparent from the following detailed description which goes with the accompanying drawings.

DESCRIPTION OF THE PREFERRED EMBODIMENTS

Figure 1:
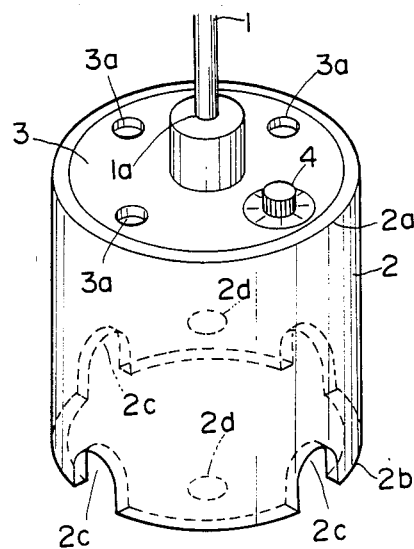
FIG. 1 is an explanatory view for explaining an embodiment of the light ray radiation device for use in medical treatment as previously proposed by the present application.

FIG. 1 is a construction view for explaining an embodiment of a light ray radiation device for use in medical treatment previously proposed by the present applicant. In FIG. 1, 1 is an optical conductor cable. The solar rays or the artificial light rays are guided into the optical conductor cable 1 at the end portion thereof not shown in FIG. 1, and the guided light rays are transmitted therethrough. The light rays corresponding to the visible light ray components of the sun's rays (the white-colored ones) are transmitted into the optical conductor cable 1 in the manner previously proposed by the present applicant in various ways. In FIG. 1, 2 is a semi-transparent cylindrical member furnished at the light-emitting end 1a of the afore-mentioned optical conductor cable 1, and 3 is a cover member for closing one end 2a of the cylindrical member 2. The light-emitting end portion side 1a, of the optical conductor cable 1, is attached to the cover member 3 at approximately the central portion thereof. The solar ray energy transmitted through the optical conductor cable 1 is discharged into the cylindrical member 2. At the time of administering medical treatment, the other end 2b of the cylindrical member is put on the part of the patient to be treated, or the same is placed opposite that same part at the desired interval therefrom. The light rays consisting of the visible light ray components transmitted through the optical conductor cable 1 in such a manner as mentioned before are radiated onto a diseased part, a desired portion, or another portion needing treatment. The light rays to be radiated onto a diseased part of a patient are the light rays corresponding to the visible light ray components of the sun's rays. Consequently, it becomes possible to administer medical treatment without exposing a patient to the harmful effects of ultraviolet or infrared rays.

Figure 2A:
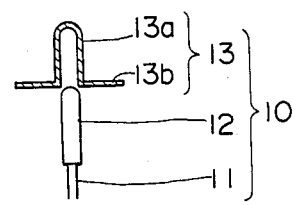
FIG. 2a and FIG. 2b are explanatory views for explaining embodiments of the light ray radiation device for use in medical treatment according to the present invention.
Figure 2B:
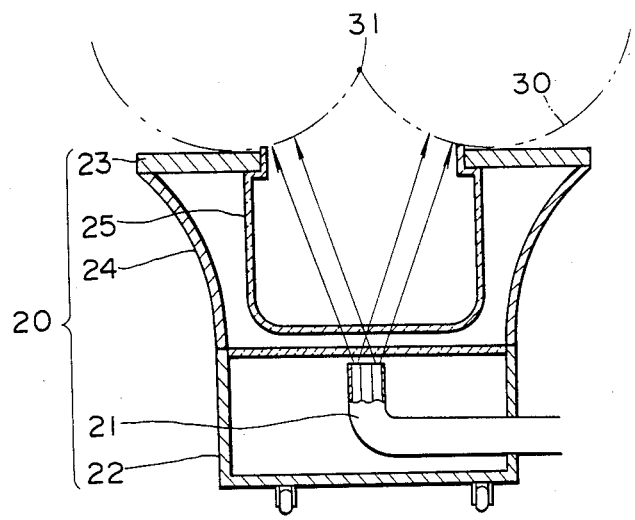

FIG. 2a and FIG. 2b are construction views for explaining embodiments of the visible light ray radiation device for use in medical treatment according to the present invention. In FIG. 2a and 2b, 10 and 20 are respectively embodiments of the visible light ray radiation device for use in medical treatment according to the present invention, and 30 is the diseased part of a human body to be cured. The device shown by 10 is employed for administering medical treatment for piles (hemerrhoids) or fungous tumors, or injury scars which remain after an operation. The method of treatment is to insert the device into the anus or cavity (vagina) 31 and radiate the visible light rays into the anus or cavity. On the other hand, the device shown by 20 is employed for administering medical treatment for piles or the like by radiating the visible light rays into the anus, the cavity, or neighboring areas of the patient who is sitting on the urinal-pot seat. Those devices, 10 and 20, are independently employed respectively. Preferably, both of those devices can be employed at the same time. At first, the light rays are radiated by means of a device 20 into the anus or cavity and neighboring areas of the patient sitting on the urinal-pot in order to lessen the pain caused by piles or other like diseases. Afterwards, the device 10 is employed for radiating light rays onto the inner surfaces of the anus or cavity by inserting the same therein.

The device 10 consists of an optical conductor cable 11, a light radiator 12, a cover member 13, and so on. The light rays corresponding to the visible light ray components of the solar rays are guided into the optical conductor cable 11 from the end portion thereof not shown in FIG. 2a. The light rays guided in such a way are transmitted through the optical conductor cable 11.

Figure 3:
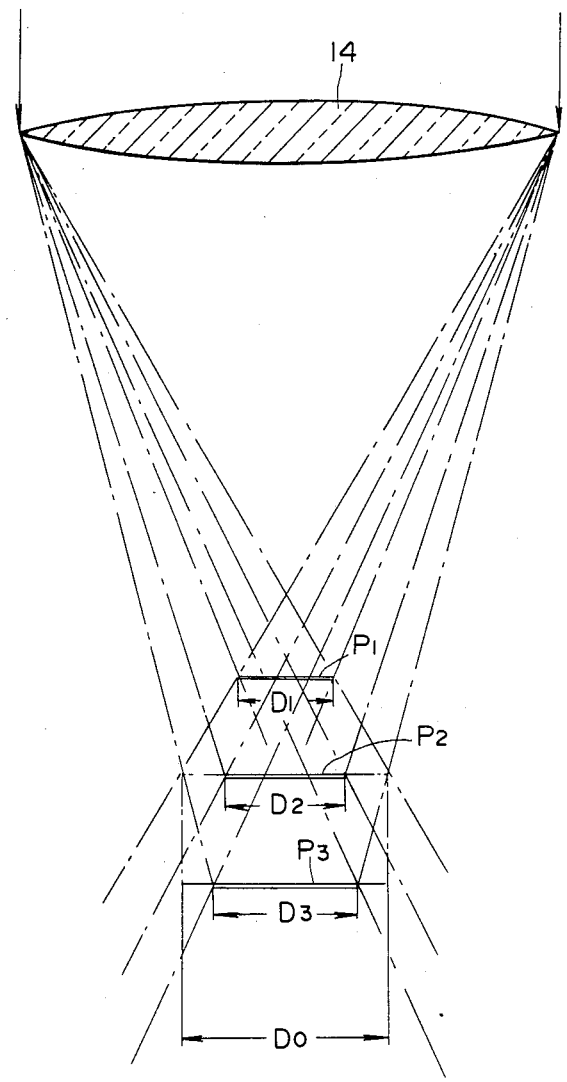
FIG. 3 is a visual explanatory view for explaining an embodiment of the visible light ray collecting method as applied to the present invention.

FIG. 3 is an explanatory view for explaining an embodiment of the device for guiding the afore-mentioned light rays, corresponding to the visible light ray components of solar rays, into the optical conductor cable. In FIG. 3, 14 is a lens system consisting of a Fresnel lens or the like, and focused by the lens system 14 are guided into an optical conductor cable for transmitting the guided solar rays therethrough. In the case of focusing the solar rays by use of a lens system, the solar image has a central portion consisting of almost white-colored light rays and a circumferential portion containing therein a large amount of light ray components consisting of the needed wave lengths for focusing the lens system.

Namely, in the case of focusing the solar rays, its focal position and the size of the solar image will vary in accordance with the wave length of the light rays. For instance, the light rays of the color blue, having a short wave length, make a solar image of diameter $D_1$ at position $P_1$. Furthermore, the light rays of the color green make a solar image of diameter $D_2$ at position $P_2$ and the light rays of the color red make a solar image of diameter $D_3$.

Consequently, as shown in FIG. 3, when the light-receiving end-surface of the optical conductor cable is put at position $P_1$, it is possible to collect solar rays containing plenty of light rays of the blue color component at the circumferential portion. When the same is put at position $P_2$, it is possible to collect solar rays containing plenty of light rays of the green color component at the circumferential portion. When the same is put at position $P_3$, it is possible to collect solar rays containing plenty of light rays of the red color component at the circumferential portion. In each case, the diameter of the optical conductor cable, is determined by the light ray components to be collected. Therefore the diameter thereof is $D_1$, $D_2$ or $D_3$, depending on the color of the light rays stressed. In such a way, the use of the optical conductor cable can be reduced, and thereby solar rays containing plenty of light rays of the desired color can be collected most effectively. And further, as shown in FIG. 3, if the diameter of the light-receiving end-surface of the optical conductor cable is enlarged to $D_0$, it is possible to collect visible light rays containing all of the wave length components.

The visible light rays transmitted through the optical conductor cable 11 in such a manner as mentioned above are guided into the light radiator 12 and discharged almost uniformly in a circumferential direction by the action of the light radiator 12. Therefore, if the light radiator 12 is inserted into the anus or the cavity 31, the light rays can be radiated onto the diseased part of the anus or the cavity 31, and thereby the pain of the diseased part can be lessened. Furthermore, the skin surface of the diseased part can be stimulated in order to help cure the disease.

On that occasion, the light radiator 12 is removably attached to the optical conductor cable 11. As a result, since the light radiator 12 can be detached from the optical conductor cable 11 in order to clean and disinfect it, it may be possible to employ the same in a sanitary way since a cover member 13 for covering the light radiator 12 is provided at the time of its use.

The cover member 13 is constructed of a transparent, soft and resilient material, and formed in the shape of a hat. Specifically, the cover member consists of an elongated bag-shaped portion 13a for inserting into the light radiator 12 and a swordguard-shaped portion 13b which spreads out at the base of the bag-shaped portion 13a. At the time of employing the light radiator 12, the same is covered by the cover member 13 so that it doesn't become dirty. And further, since the filth or the like emerging out of the diseased part is stopped and caught by the swordguard-shaped portion 13b, the outer circumferential portion of the light radiator 12 is also not soiled.

Furthermore, since the light radiator 12 can be prevented from being inserted too deeply into the anus or the cavity 31 by the swordguard-shaped portion 13b, it may be possible to administer medical treatment to piles or fungous tumors in the cavity by stably inserting the light radiator 12 into the anus or the cavity without giving the patient reason to worry. The cover member 13 is made to be disposable. However, if it is cleaned and disinfected it can be used repeatedly.

Figure 4:
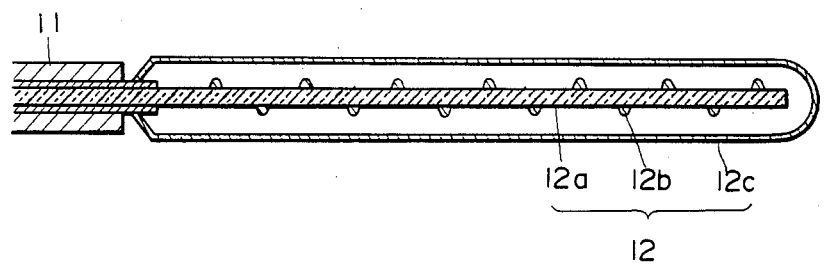
FIG. 4 is an explanation of an embodiment of the light radiator employed with the present invention.

FIG. 4 is an explanatory view for explaining an embodiment of the afore-mentioned light radiator 12. It may be easily understood that the light radiator employed in the present invention is not limited to the one shown in FIG. 4, and that other light radiators already proposed by the present applicant in various ways can also be employed.

In FIG. 4, the light radiator 12 consists of an optical conductor 12a, a layer of adhesive such as epoxy resin 12b uniformly bonded to the outer circumferential portion of the optical conductor 12a and having the refractive index equal to or larger than that of the optical conductor 12a, and a transparent cover member 12c for covering the otical conductor 12a, to which adhesive 12b is bonded. The light radiator 12 is connected with the light-emitting end of the optical conductor cable 11 and employed for radiating light rays at the time of administering medical treatments.

Consequently, the light rays transmitted through the optical conductor cable 11 are guided into the optical conductor 12a of the light radiator 12 and propagate through the optical conductor 12a toward the tip end portion thereof. During the time of its propagation, the light rays are refracted in the adhesive layer portion 12b and discharged outside of the optical conductor 12a. The light rays radiated in such a way are employed for administering medical treatment for piles or other like diseases as mentioned before. Needless to mention, various sizes and shapes of the light radiator 12 are provided in accordance with the purpose of its use and the physical shape of the patient. An appropriate light radiator is selected among them and employed.

In FIG. 2b, 20 shows another embodiment of the light ray radiation device for use in medical treatment and according to the present invention. The device 20 consists of an optical conductor cable 21 for receiving the light rays corresponding to the visible light ray components of the sun which are to be guided thereinto and for transmitting the same therethrough in the same manner as is the case of the afore-mentioned optical conductor cable 11, a supporting block 22 for removably fixing and supporting the light-emitting end of the optical conductor cable 21, a urinal-pot seat, on which a patient 30 sits, and a connecting member 24 for unitarily connecting the urinal-pot seat with the supporting block 22 and for fixedly supporting the light-emitting end portion of the optical conductor cable.

When the patient 30 sits on the urinal-pot seat 23, the light rays discharged from the light-emitting end of the optical conductor cable 21 impinge on the anus, or the cavity, or the neighboring area of the patient 30. Therefore, when the patient suffering from the piles sits on the urinal-pot seat 23, the light rays discharged from the optical conductor cable 21 can be radiated into the anus, or the cavity, or the neighboring areas of the patient. Therefore, it may be possible to ease the pain of piles or other like diseases and to administer medical treatment for piles or other like diseases.

On that occasion, if the inner circumferential (surface) portion is formed in the state of a reflecting surface, the light rays leaking from the optical conductor cable 21, etc. can be reflected thereon and directed toward the anus, or the cavity, or the neighboring areas. And further, the upper surface of the supporting block 22 for supporting the light-emitting end of the optical conductor cable is covered by the use of a light-passing (transparent) member for the purpose of preventing the optical conductor cable 21 or other parts from getting dirty by the filth emerging out of the diseased part of the patient. Otherwise, a transparent cover member 25, as shown in FIG. 2b, is removably attached to the urinal-pot seat, and the filth emerging out of the diseased part is received by the cover member 25. Afterwards, the cover member 25 is cleaned and disinfected. In such a way, the device for use in medical treatment can be employed more sanitarily.

Furthermore, the device 20 has casters and the optical conductor cable 21 is removably attached to the supporting block 22 for supporting the light-emitting end of the optical conductor. Consequently, when the device 20 is not employed, the optical conductor 21 can be detached from the supporting block 22, and thereby both of the separated portions can be cleaned up in the optional desired places, respectively. As a matter of course, the device 20 and the afore-mentioned device 10 can be independently employed respectively, or both of those devices can be employed at the same time. For the sake of employing the devices in two ways, notches are formed at the front side and the rear side of the cover member 25, in order to enable the afore-mentioned device 10 to be taken out from and put into the cover member 25.

As is apparent from the foregoing description, according to the present invention, the medical treatment for piles, fungous tumor in the cavity or an injury scar caused by excising such a fungous tumor in the cavity, can be administered without giving the patient pain and allowing him (or her) to be very comfortable by being in a sitting position.

I claim:

1. A solar light ray radiation device for use in medical treatment comprising an optical conductor cable for conducting light rays corresponding to the visible light ray component of solar rays, said cable having a light-emitting end, an elongated light radiator means detachably connected to said cable at said light emitting end, said light radiator means comprising an optical conductor joined to said light emitting end of said cable, a layer of adhesive uniformly bonded to the outer circumferential portion of said optical conductor, said adhesive having a refractive index equal to or larger than that of said optical conductor, a transparent cover means extending about said optical conductor, said optical conductor being completely enclosed within said transparent cover means, said transparent cover means being spaced from said optical conductor, a disposable resilient cover member disposed about and tightly fitted onto said cover means, said disposable cover member being made of a transparent material, said disposable cover member being elongated and having one longitudinal end which is closed and the other longitudinal end which is open to receive said cover means, said other longitudinal end having a radial extending flange portion extending radially outwardly from said other longitudinal end, said disposable cover member being disposed over said cover means during use of said light radiation device in a body cavity and being removeable from said cover means and disposed of upon completion of said use, whereupon another like cover member can be employed for subsequent use of the light radiation device.

2. A solar light ray radiation device for use in medical treatment comprising an optical cable for conducting light rays corresponding to the visible light rays component of solar rays, said cable having a light-emitting end portion, supporting block means for removably supporting said light-emitting end portion, a pot seat means on which a patient to be treated is seated, connecting structure means unitarily connecting said pot seat means with said supporting block means, said connecting structure means underlying said pot seat means, said supporting block means underlying said connecting structure means, said pot seat means having a central opening, said light-emitting end portion having a light-emitting end means which underlies said central opening and which emits said light rays toward said central opening, a transparent cover member mounted on said pot seat means, said cover member having a bottom wall portion and an upright wall portion extending from said bottom wall portion and connected to said port seat means, said bottom wall portion underlying said central opening and overlying said light-emitting end means such that said light rays emitted from said light-emitting end means toward said central opening pass through said bottom wall portion.

3. A solar light ray radiation device according to claim 2 further comprising reflective means on an inside surface of said connecting structure means.

* * * * *